US00PP34570P3

(12) United States Plant Patent
Keller-Janssen

(10) Patent No.: US PP34,570 P3
(45) Date of Patent: Sep. 13, 2022

(54) ***ARMORACIA RUSTICANA* PLANT NAMED 'K-62'**

(50) Latin Name: *Armoracia rusticana*
Varietal Denomination: 'K-62'

(71) Applicant: HRP, LLC, Collinsville, IL (US)

(72) Inventor: Lindsey Keller-Janssen, Collinsville, IL (US)

(73) Assignee: HRP, LLC, Collinsville, IL (US)

( * ) Notice: Subject to any disclaimer, the term of this patent is extended or adjusted under 35 U.S.C. 154(b) by 0 days.

(21) Appl. No.: 16/873,661

(22) Filed: Feb. 27, 2020

(65) Prior Publication Data

US 2021/0274695 P1 Sep. 2, 2021

(51) Int. Cl.
*A01H 5/06* (2018.01)
*A01H 6/20* (2018.01)
*A01H 4/00* (2006.01)

(52) U.S. Cl.
USPC ..... Plt./258
CPC ..... *A01H 6/20* (2018.05); *A01H 4/005* (2013.01)

(58) Field of Classification Search
USPC ..... Plt./258
CPC ..... A01H 5/02; A01H 5/06
See application file for complete search history.

*Primary Examiner* — Kent L Bell
(74) *Attorney, Agent, or Firm* — Thompson Coburn LLP

(57) ABSTRACT

A new and distinct horseradish (*Armoracia rusticana*) named K-62 is disclosed, characterized by and distinguished from prior commercial horseradish varieties by increased activity of horseradish peroxidase (HRP). Plants have been clonally propagated by root division and shown to retain the increased HRP activity, which can be used, among other things, in molecular biology applications.

4 Drawing Sheets

Botanical classification: *Armoracia rusticana.*
Variety denomination: 'K-62'.

BACKGROUND

Horseradish (*Armoracia rusticana*, syn. *Cochlearia armoracia*) is a plant of the Brassicaceae family. It can be planted as an annual or perennial crop. It is a root vegetable used in culinary applications for its sharp, pungent taste. Horseradish is genetically highly heterogenous and seedlings from heterogeneous crosses yield plants that are genetically dissimilar. Thus, in order to maintain fixed genetics, commercial horseradish plants are generally asexually propagated.

In addition to its culinary uses, horseradish is a source of Horseradish Peroxidase (HRP), an enzyme found in horseradish plants that has uses in numerous medical and scientific applications. HRP is used extensively in molecular biology and biochemistry testing for its ability to increase the detectability of target molecule by signal amplification.

HRP is primarily found in root tissues with limited amounts found in leaf petioles and lead blades. Horseradish varieties differ in their relative amounts of HRP found in their roots. It is advantageous to have a horseradish plant that produces enhanced levels of HRP to permit the production of greater amounts of HRP, for example, with less harvested roots.

The new cultivar named 'K-62' is the product of a breeding program initiated to develop horseradish varieties with increased levels of HRP. Horseradish roots were asexually propagated by planting root sections (referred to as "sets") collected from a prior crop. Two varieties of horseradish plants, 1573 and 315, (not patented) were crossed. These horseradish crowns were forced to flower and were hand-crossed in a greenhouse setting. The resulting seedlings were grown in field conditions and harvested after a normal growing season. The seedlings were subsequently assayed for HRP levels. 'K-62' contains a higher level of HRP activity in the root than any commercially available horseradish plant known to the Inventor. 'K-62' yielded 194.5 units of HPR per gram of horseradish root tissue, which is over three times the amount of HRP as any other commercially available horseradish plant known to the Inventor.

Asexual reproduction of 'K-62' horseradish plant by root division in a controlled greenhouse environment in Collinsville, Ill., since November 2019, has shown that the unique characteristics of this new horseradish plant are stable and reproduced true to type in successive generations.

SUMMARY

The new cultivar 'K-62' has not been observed under all possible environmental conditions. The phenotype may vary somewhat with variations in environment such as temperature, day length, and light intensity, without, however, a change in the genotype of the plant.

The following traits have been repeatedly observed and are determined to be the unique characteristics of the new cultivar 'K-62'. 'K-62' plants are similar to other horseradish in most horticultural characteristics, however, these characteristics in combination distinguish 'K-62' as a new and distinct horseradish cultivar:

1. Significant HRP activity observed in the roots.
2. Dark green leaves.
3. Short stature.

BRIEF DESCRIPTION OF THE FIGURES

The accompanying photographs illustrate the overall appearance of the new cultivar 'K-62' grown in Collinsville, Ill., in a field and under commercial horseradish production practices during the spring/summer. 100/50/300 units of fertilizer were applied prior to planting. Fields were hand hoed to remove weeds and sprayed with HERO® insecticide for insects. Plants were about four to five months old when the photographs were taken. During the production of the plants, day temperatures ranged from 65 degrees to 85 degrees Fahrenheit and night temperatures ranged from 45 degrees to 60 degrees Fahrenheit. Plants received an adequate amount of rain for the soil type in the field and other weather conditions.

Figure 1:
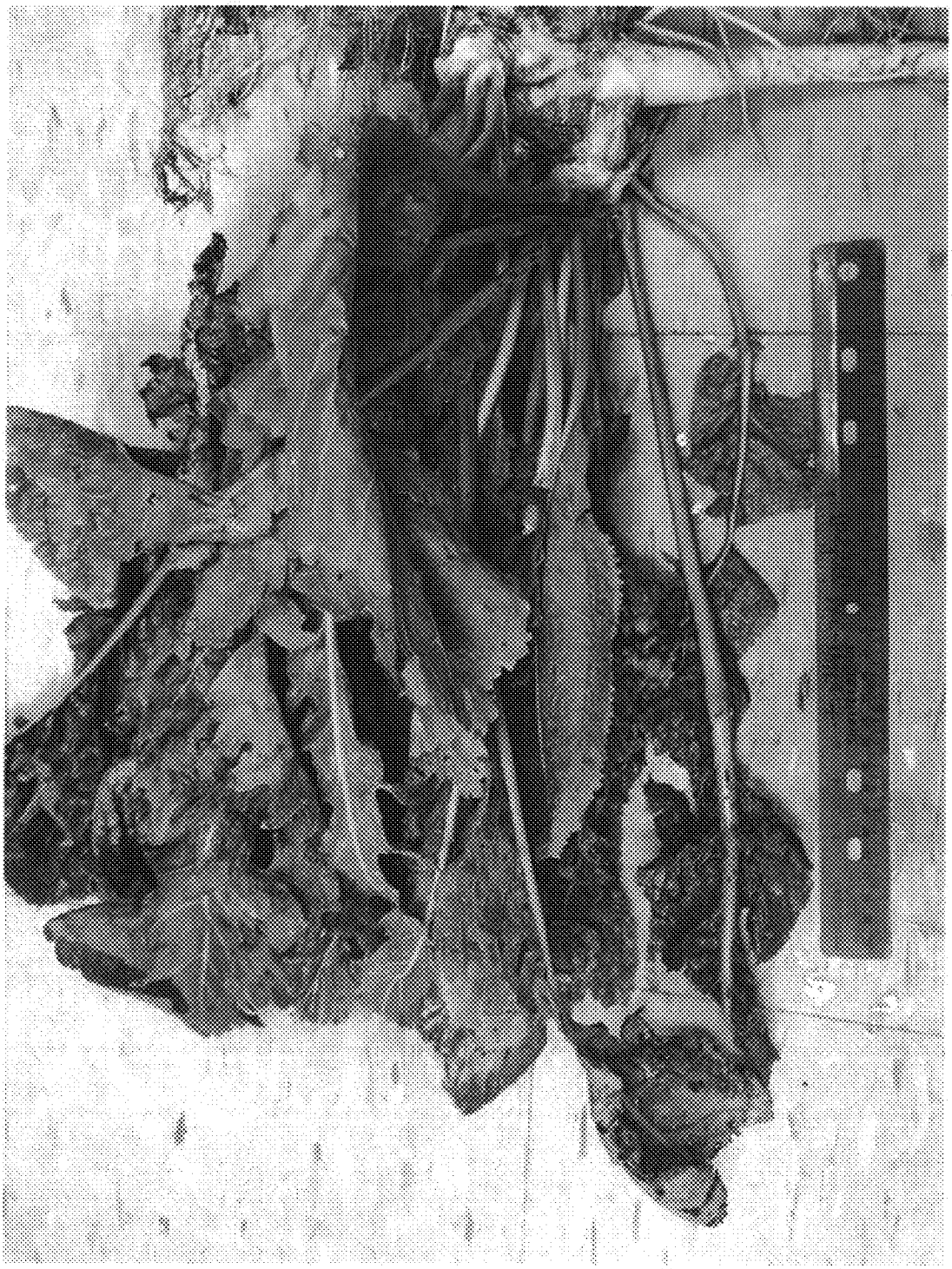
FIG. 1. The photograph in FIG. 1 provides a side view of 'K-62' foliage.
Figure 2:
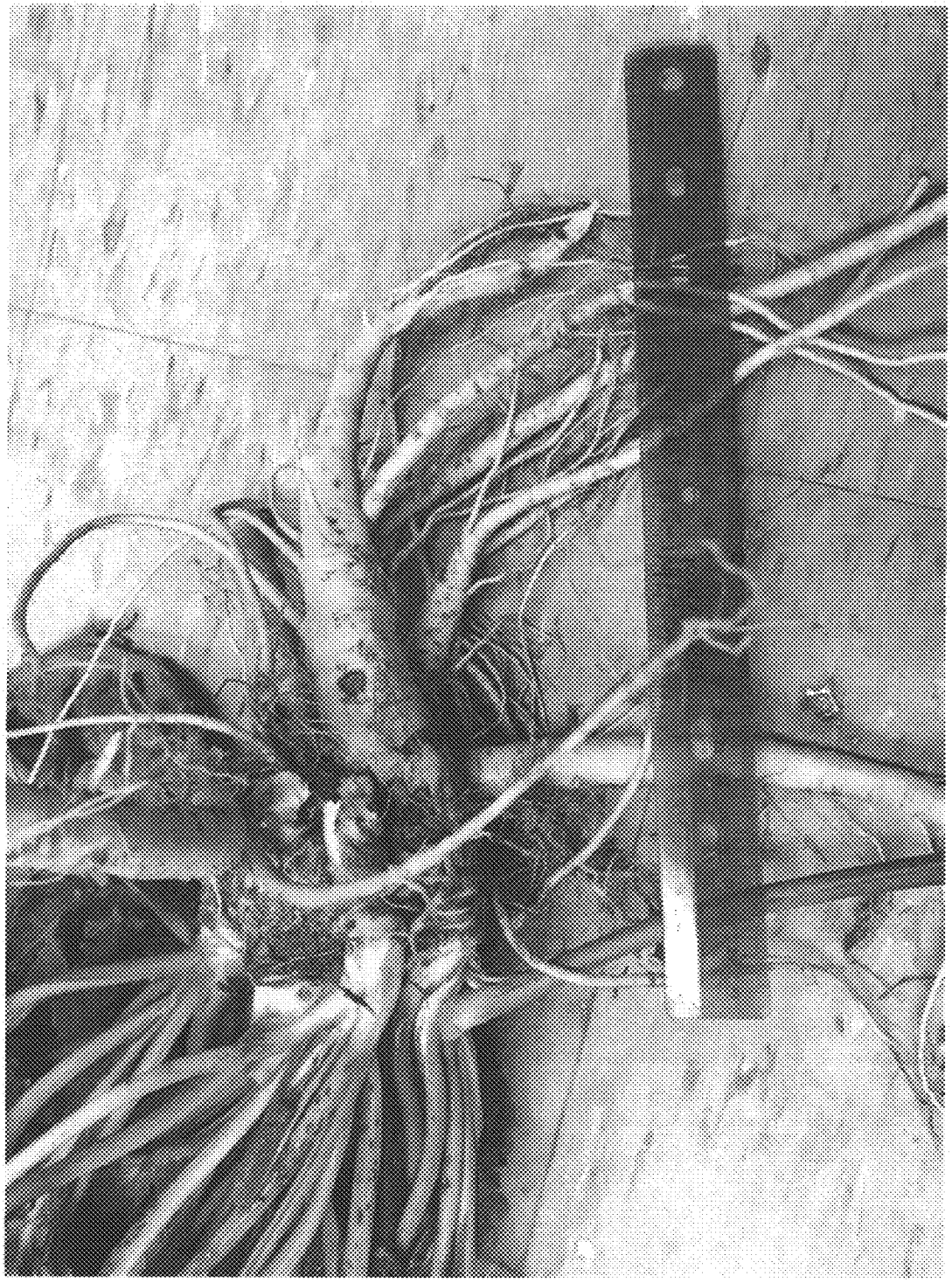
FIG. 2. The photograph in FIG. 2 provides a side view of 'K-62' root structure.
Figure 3:
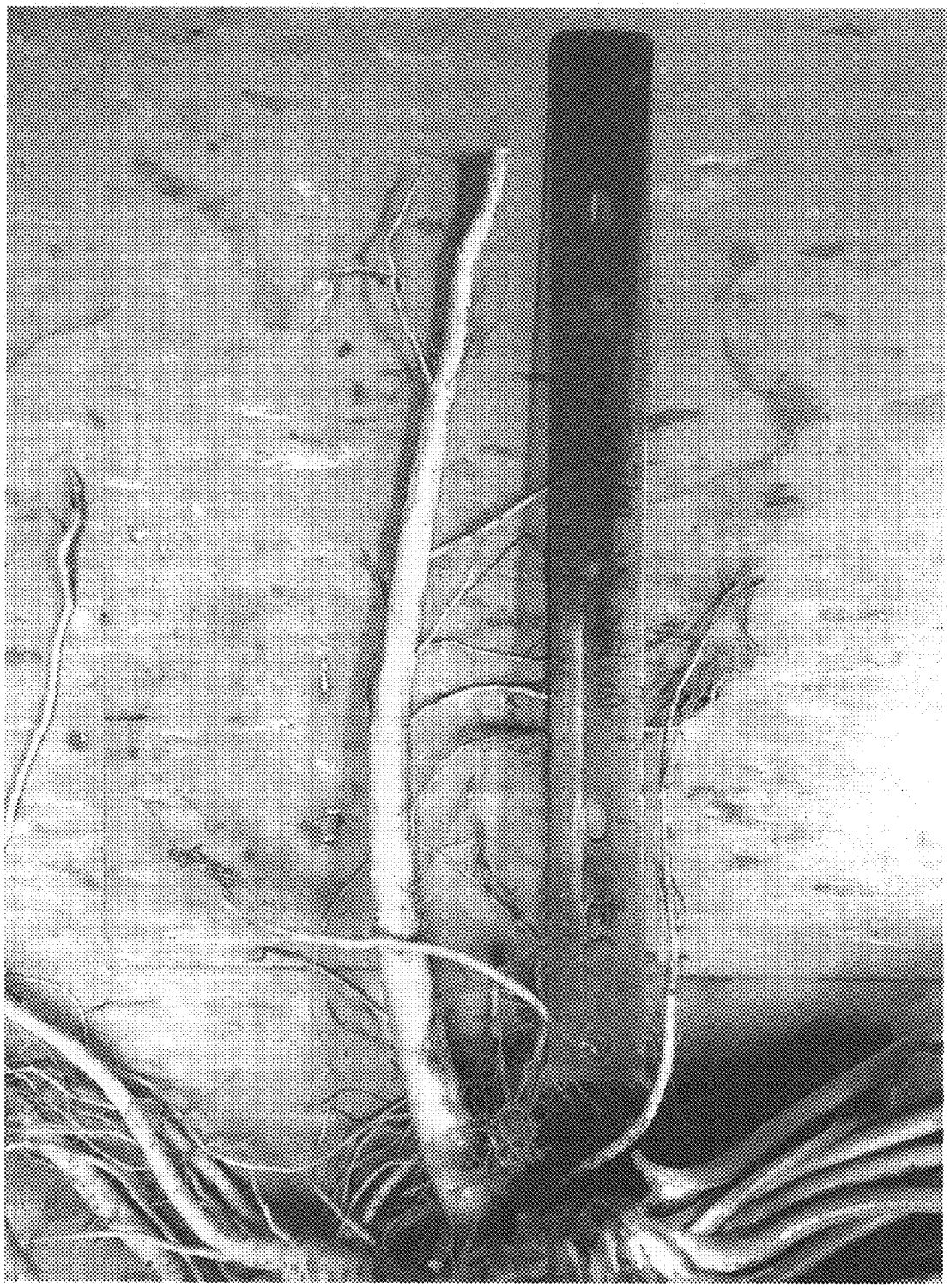
FIG. 3. The photograph in FIG. 3 provides a view of an isolated 'K-62' root.
Figure 4:
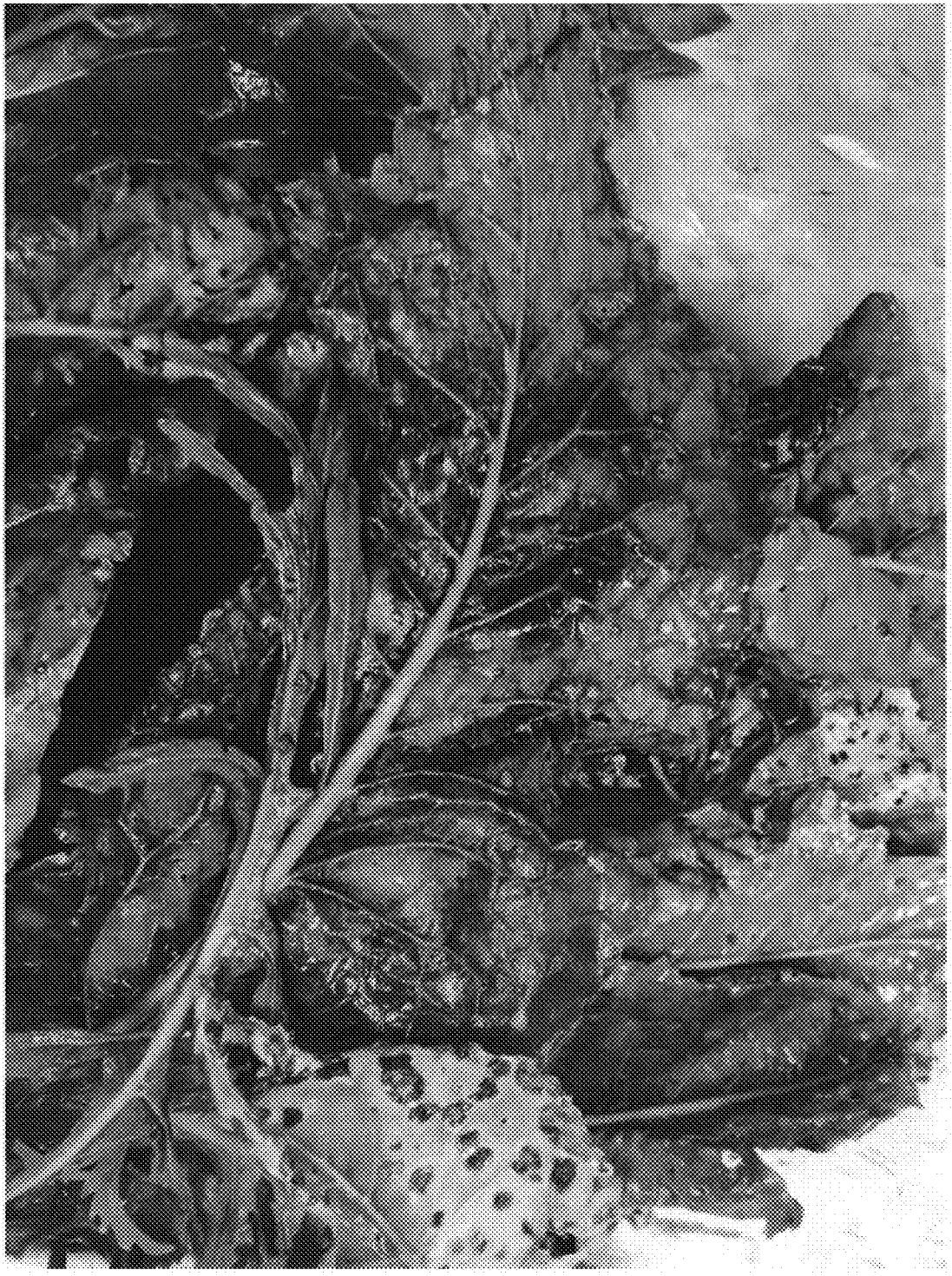
FIG. 4. The photograph in FIG. 4 provides a close-up view of 'K-62' foliage.

The photographs were taken using conventional techniques and although colors may appear different from actual colors due to light reflectance, the colors are as accurate possible using conventional techniques.

DETAILED BOTANICAL DESCRIPTION

The following observations and measurements describe the new cultivar 'K-62', grown in Collinsville, Ill., in a field and under commercial horseradish production practices during the spring/summer. 100/50/300 units of fertilizer were applied prior to planting. Fields were hand hoed to remove weeds and sprayed with HERO® insecticide for insects. Plants were about four to five months old when the photographs were taken. During the production of the plants, day temperatures ranged from 65 degrees to 85 degrees Fahrenheit and night temperatures ranged from 45 degrees to 60 degrees Fahrenheit. Plants received an adequate amount of rain for the soil type in the field and other weather conditions. The plants as described were four to five months of age. Measurements and numerical values represent averages of typical plants. In the following description, color references are made to The Pantone Book of Color (1990).

Botanical classification: *Armoracia rusticana* 'K-62'.

Propagation:

*Method*.—Root division.

*Time to initiate roots*.—About four weeks at approximately 70 degrees F.

*Time to produce a rooted young plant*.—About six weeks at approximately 70 degrees F.

*Growth*.—Tolerates wet soil and grows vigorously.

*Root description*.—Stout taproot and stout rhizomes with finer rootlets. Fleshy taproot averaging 10-12 inches in length and 1-2 inches in diameter, and having a cylindrical and tapered shape. Semi-rough skin that is thin, covered in gnarled notches and bumps, and ranges in color from tan (12-0910) to light brown (13-1011). Underneath the skin's surface, the flesh is white (11-0105), dense, crisp, and contains liquid. Root has a sharp, pungent taste.

Horseradish plant:

*Growth habit*.—Inverted triangle. Basal leaves are widely spreading and can be floppy.

*Height*.—On average approximately 18 to 42 inches.

*Plant spread*.—On average approximately 18 to 36 inches.

*Branching characteristics*.—Rosette of basal leaves from which there develops one or more flowering stalks. Central stalk and upper axillary stems have alternate leaves and terminate in racemes or panicles of flowers.

*Peduncles*.—Light green (13-0215) to medium green (16-0233) in color and glabrous. The peduncles have a typical and observed length of 125 centimeters and diameter of 2-3 centimeters.

Foliage:

*Leaf*.—

*Average length*.—Basal leaves approximately 12 to 18 inches. Alternate leaves approximately 1 to 6 inches.

*Average width*.—Basal leaves approximately 1.5 to 6 inches across. Alternate leaves approximately ¼ to 2 inches across.

*Shape of blade*.—Basal leaves are broadly oblong-elliptic. Edges are wavy with small, rounded teeth. Alternate leaves are narrowly elliptic to broadly oblong-lanceolate and grow from stems. Alternate leaves become smaller, narrower and shorter stalked further up the stem and upper leaves can be lance-linear with coarsely crenate-serrate to shallowly pinnatidid margins and sessile or with short petioles. The basal and alternate leaves are arranged on the stem in an alternate pattern. The leaves have long petioles, are obovate to oblanceolate, attenuate to cuneate at the base, unevenly crenate, and grow to a length of up to 100 centimeters. Leaves on the inflorescence stem are oblanceolate to linear in shape.

*Texture of surface*.—Both upper and lower surface of basal and alternate leaves are glabrous.

*Color*.—Upper surface of both basal and alternate leaves are medium green (15-0332) to dark green (18-0125) in color. Lower surface of both basal and alternative leaves are paler shade of green than upper surface.

Petiole:

*Length*.—The petioles of the basal leaves can be approximately as long as the blades. The typical and observed petiole diameter is 6 millimeters.

*Texture*.—Glabrous, smooth.

*Color*.—Light green (15-6322).

Flower:

*Blooming period*.—From mid-spring to mid-summer and lasts about 2 months with 3-7 blooms per plant. There are generally between 1000 to 2000 flowers per inflorescence. The inflorescence has numerous flowers that continue to open over a period of several days, with individual flower longevity being 1-2 days, depending on prevailing weather conditions, with hot conditions resulting in less longevity.

*Location*.—The flowers bloom toward the apex of each raceme (or branch of a panicle). The inflorescence is a panicle or compound raceme with a branching axis that is 15 to 20 centimeters in diameter and 25 to 35 centimeters in length.

*Petals*.—The plant bears solitary flowers on panicles with four white (11-0507) petals. Petals are about twice the length of the sepals. The petals are broadly obovate in shape and have a smooth texture. The petals form the shape of a cross for the flower. The flowers are 8-10 millimeters in diameter with a 2 millimeter depth. Individual flower petals are 6 millimeters long and 4 millimeters wide.

*Sepals*.—Four light green (12-6204) sepals. The typical and observed length is 4 millimeters and the typical and observed width is 2 millimeters. The sepals are concave, have a smooth texture, and are broadly ovate with a membranous white margin.

*Stamens*.—Six.

*Pistil*.—Short style.

*Pedicels*.—Ascending pedicels are ¼ to ¾ inches in length, light green (12-6204), and glabrous.

Fruit/seeds:

*Shape*.—Flowers are replaced by cylindrical seedpods.

*Size*.—Seedpods are up to ¼ inch long. Seedpods are light green (17-0235), are typically 4-7 millimeters long and 1-2 millimeters in diameter.

*Number*.—Each seed pod can contain up to approximately 8 seeds.

Other characteristics:

*Disease and pest resistance*.—Some resistance to internal root discoloration.

*Temperature tolerance*.—Tolerant to wind, rain, and temperatures ranging from about 20 degrees F. (ground temperature) to 100 degrees F.

*Culinary*.—Horseradish can be used as a spice or culinary herb, especially utilizing its pungent tasting roots.

*Toxicity*.—Because of high levels of mustard oil from the conversion of glucosinolates, especially in the root, ingestion of horseradish can produce toxic effects on mammalian herbivores.

*Horseradish peroxidase* (*HRP*) *activity*.—As determined, for example in the following Examples, 'K-62' yielded 194.5 units of HPR per gram of horseradish root tissue, which is over three times the amount of HRP as any other commercially available horseradish plant known to the Inventor.

The following examples are included to demonstrate certain embodiments of the disclosure. It should be appreciated by those of skill in the art that the techniques disclosed in the examples which follow represent techniques discovered by the inventor to function well in the practice of the disclosure. However, those of skill in the art should, in light of the present disclosure, appreciate that many changes can be made in the specific embodiments which are disclosed and still obtain a like or similar result without departing from the spirit and scope of the disclosure.

EXAMPLES

Horseradish Extraction Procedure to Determine Peroxidase Content

Equipment and Supplies:

Cleaver for chopping roots

Vegetable Peeler

Cutting Board

Balance to weigh samples 1 gal. WARING® blender 1 liter blender 80 oz. Poly bottles to hold all samples. (pre-labeled with sample identification)

Cheese Cloth (About 5"×8.5")

Funnel 250 ml Erlenmeyer flask

Procedure:

1. Receive the horseradish Root samples, if there is enough time to process samples proceed with remainder of this procedure, if not keep horseradish roots in refrigerator until procedure can be run.

2. Wash each sample of roots separately with water to remove dirt/mud that will be on root.

3. Record the appearance of each root sample on data sheet also record identity of each root sample. For example: variety, Plot 2 with dry soil can be coded as such: (Use Lab Data Sheet). Also take pictures to compare.

4. Provide sample number for each root and record it on Lab Data Sheet.

5. Chop each root sample separately using cleaver (note: preferred hand protection is Metal mesh glove). Chop into small ¼"-½" pieces. Take a picture for record. Record on Data sheet the appearance of the chopped root, ex: rot present, brown ring, white color.

6. Weigh each sample of chopped roots separately. Weigh approx. 40 grams (454 grams SA=1 lb) of chopped roots and place into appropriate Poly jar that is labeled with sample ID. Record weigh of sample on data sheet.

a. Step 6-9 should proceed with an equal time interval (10-15 min.) between each sample processed.

7. Place the pre-weighed sample of chopped horseradish root sample into a 1 gal. SS Waring blender. Use a blender bowl that has sharp blending blades.

8. Add 1 liter/pound of root sample in blender bowl (other proposal has 100 ml for 40 g), secure bowl lid and blend on high speed for 30 seconds. Then rinse the sides of the blender with DI water, blend for 30 more seconds (note: weighed the bottle of water before and after the rinses to try and get a more exact measurement of water used).

9. Pour off top blended slurry into labeled container. Rinse the sides of the blender and pour the liquid into the container.

10. Repeat Step 6-9 until all samples are processed.

11. Allow samples to set in cold room for 1 hour.

12. When the 1 hour time has elapsed take each sample in same sequence that it was blended and filter through cheesecloth using a funnel and the Erlenmeyer flask. Periodically squeeze the pulp through the cloth to get as much liquid as possible. When no more liquid can be squeezed from the excessive pulp, measure the amount of liquid filtered from the blended mixture, record it onto the data sheet and then pour the liquid into a CLEAN container.

13. Assay each sample for Peroxidase Activity, following this set of parameters when assaying samples:

A. Prepare all Assay reagent that need to be made fresh just prior to starting assays.

B. Dilute sample as necessary for assay based on requirements of assay procedure. Once correct dilution is established use same dilution for all other samples.

C. Assay a Peroxidase Control at least once during running assay of samples to Confirm validity of assay.

14. Record assay results in data sheet and complete data sheet.

Enzymatic Assay of Peroxidase (EC 1.11.1.7)

Description

This procedure is for the determination of Peroxidase enzymatic activity using Pyrogallol as the substrate. The continuous spectrophotometric rate determination ($A_{420}$, Light path=1 cm) is based on the following reaction:

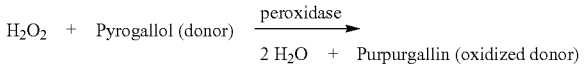

Unit Definition: One unit of peroxidase will form 1.0 milligram of purpurogallin from pyrogallol in 20 seconds at pH 6.0 at 20° C. This purpurogallin (20 second) unit is equivalent to ~18 μM units per minute at 25° C.

Precautions

Please consult the Safety Data Sheet for information regarding hazards and safe handling practices.

Reagents and Equipment

Potassium Phosphate, Monobasic, Anhydrous

Hydrogen Peroxide, 30% (w/w) Solution

Pyrogallol

Cuvettes and thermostatted spectrophotometer

Preparation Instructions (Storage/Stability)

1. Use ultrapure water (≥18 M∩$^{X}$ cm resistivity at 25° C.) for the preparation of reagents.

2. Phosphate Buffer (100 mM Potassium Phosphate Buffer, pH 6.0 at 20° C.)—Prepare a 13.6 mg/ml solution of Potassium Phosphate, Monobasic, Anhydrous using ultrapure water. Adjust pH to 6.0 at 20° C. with 1.0 M KOH.

3. After adjusting the pH. Peroxide Solution (0.50% [w/w] Hydrogen Peroxide [$H_2O_2$] Solution)—Prepare 5 ml of a 1:60 solution in ultrapure water using Hydrogen Peroxide, 30% (w/w) Solution (PREPARE FRESH and store the solution in a capped 4 dram vial).

4. Pyrogallol Solution (5% [w/v] Pyrogallol Solution)—Prepare a 50 mg/ml solution in ultrapure water using Pyrogallol. PREPARE FRESH AND KEEP FROM LIGHT. Peroxidase Solution—Prepare a 10 mg/ml solution of peroxidase in COLD Phosphate Buffer. At this concentration, the solution is stable for 15 minutes.

5. Immediately before use, prepare a working solution containing 0.4-0.7 unit/ml of Peroxidase in COLD Phosphate Buffer.

Procedure

Final Assay Concentrations—In a 3.00 ml reaction mix, the final concentrations are 14 mM potassium phosphate, 0.027% (w/w) hydrogen peroxide, 0.5% (w/v) pyrogallol, and 0.04-0.07 unit peroxidase.

1. Pipette the following reagents into suitable cuvettes:

| Reagent | Test Sample (ml) | Blank (ml) |
|---|---|---|
| Ultrapure Water | 2.10 | 2.10 |
| Phosphate Buffer | 0.32 | 0.32 |
| Peroxide Solution | 0.16 | 0.16 |
| Pyrogallol Solution | 0.32 | 0.32 |

2. Mix by inversion and equilibrate for 10 minutes to 20° C. in the spectrophotometer. Monitor the $A_{420}$ until constant, using a suitably thermostatted spectrophotometer.

Then add:

| Reagent | Test Sample (ml) | Blank (ml) |
|---|---|---|
| Phosphate Buffer | — | 0.10 |
| Enzyme Solution | 0.10 | — |

3. Immediately mix by inversion and record the increase in $A_{420}$ at a rate of 1 reading/second for ~3 minutes. Use the maximum linear rate to obtain the $DA_{420}$/20 seconds for both the Test Sample and Blank.

4. The Test Sample enzyme concentration may have to be modified in order for the rate ($DA_{420}$/20 seconds) to be within the specified absorbance change rate of 0.16-0.28. (Averaged used is 5 microliters but sometimes solution has to be diluted)

Calculations $$\text{Units/ml } HRP = \frac{(\Delta A_{420}/20 \text{ sec Test Sample} - (\Delta A_{420}/20 \text{ sec Blank})(3 \text{ ml})(df)}{(12(\varepsilon(\text{Lmol}^{-1}\text{cm}^{-1}) \text{ of 1 mg/ml Purpurogallin at 420 nm})(0.1(\text{ml filtrate used}))}$$

Where:

3=Volume (in milliliters) of assay df=Dilution factor

12=Extinction coefficient of 1 mg/ml of Purpurogallin at 420 nm 0.1=Volume (in milliliters) of enzyme used

| units/ml enzyme |
|---|
| Units/mg solid = mg solid/ml enzyme / units/ml enzyme |
| Units/mg protein = mg protein/ml enzyme |
| UNIT DEFINITION: |
| One unit will form 1.0 milligram of purpurogallin from pyrogallol in 20 seconds at pH 6.0 at 20° C. This purpurogallin (20 seconds) unit is equivalent to approximately 18 mM units per minute at 25° C. |
| FINAL ASSAY CONCENTRATIONS: |
| In a 3.00 ml reaction mix, the final concentrations are 14 mM potassium phosphate, 0.027% (w/w) hydrogen peroxide, 0.5% (w/v) pyrogallol and 0.04¬0.07 unit peroxidase. |

REFERENCE:

Chance, B. and Maehly, A. C. (1955) Methods in Enzymology, II, 773-775

TABLE 1

Selected horseradish seedlings (from directed crosses) and standard varieties for HRP content in root tissue.

| Selected Horseradish Seedling/Standard Variety | HRP units/gram of root tissue |
|---|---|
| K1 (1573 × 315 − R22) | 194.5 |
| K2 (647 Open pollinated) | 136.3 |
| K3 (1573 × 315 − R24) | 136.2 |
| 9705-1 | 73.0 |
| 315-1 | 59.4 |
| 9705-2 | 57.5 |
| 315-2 | 44.7 |
| 602-1 | 38.6 |
| 315-3 | 36.2 |

TABLE 1-continued

Selected horseradish seedlings (from directed crosses) and standard varieties for HRP content in root tissue.

| Selected Horseradish Seedling/Standard Variety | HRP units/gram of root tissue |
|---|---|
| 602-1 | 29.5 |
| 9705-3 | 22.7 |

The breadth and scope of the present disclosure should not be limited by any of the above-described exemplary embodiments, but should be defined only in accordance with the following claims and their equivalents.

What is claimed is:

1. A new and distinct variety of horseradish plant, substantially as illustrated and described herein.

* * * * *